US006410817B1

(12) United States Patent
Colling et al.

(10) Patent No.: US 6,410,817 B1
(45) Date of Patent: *Jun. 25, 2002

(54) ETHYLENE RECOVERY SYSTEM

(75) Inventors: Philip M. Colling, Corpus Christi, TX (US); Raul A. Hauser Luna, Coatzacoalcos (MX)

(73) Assignee: Celanese International Corporation, Dallas, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/342,938

(22) Filed: Jun. 29, 1999

(51) Int. Cl.[7] .......................... C07C 7/11; C07C 7/148; C07C 7/00
(52) U.S. Cl. ........................ 585/866; 585/809
(58) Field of Search ................. 585/866, 809

(56) References Cited

U.S. PATENT DOCUMENTS 3,714,237 A * 1/1973 Calcagno et al. ....... 260/497 A
6,118,021 A * 9/2000 Gottschlich et al. ........ 560/243

OTHER PUBLICATIONS

The fifth edition of Perry's Chemical Engineers' Handbook, pp. 14–2 and 14–3, 1973.*
Brunner, E., "Fluid Mixtures at High Pressures," *J. Chem. Thermodynamics*, 1987, 19, 823–835.

* cited by examiner

*Primary Examiner*—Thuan D. Dang
(74) *Attorney, Agent, or Firm*—M. Susan Spiering

(57) ABSTRACT

Ethylene is a commodity chemical used as a reactant in the production of vinyl acetate. Ethylene is relatively expensive thus making its recovery and re-use in the process encouraged. The present invention provides a method for the recovery of ethylene from the inert gas purge stream from the reactor loop in a vapor-phase process for making vinyl acetate. The method of the present invention includes the steps of contacting the inert gas purge stream containing ethylene with acetic acid in an absorption vessel; discharging a stream containing acetic acid and ethylene from one aspect of the absorption vessel; separating the ethylene from the acetic acid in the stream by contacting the stream with ethylene gas in a scrubber column; and recovering ethylene from a top portion of the scrubber column. The method may also include the step of recycling the recovered ethylene to the reactor loop for further use.

8 Claims, 2 Drawing Sheets

ETHYLENE RECOVERY SYSTEM

BACKGROUND OF THE INVENTION

1. Field of the Invention

The present invention is directed to a system for recovery of ethylene from the inert gas purge stream from a vapor-phase production process, in particular, the vapor phase production process for vinyl acetate.

2. The Related Art

Although the invention is explained in terms of vapor phase production of vinyl acetate, the inventive process may be employed wherever an ethylene recovery loop process exists. For example, ethylene oxide/ethylene glycol production or production of acrylates.

Ethylene is a commodity chemical used in various chemical processes for making numerous other chemicals. Ethylene is a particularly important reactant in the vapor-phase production of vinyl acetate. Because ethylene is costly, producers of vinyl acetate by vapor-phase processes find that recovery and recycling of ethylene is an important cost saving measure.

In a vapor-phase vinyl acetate process, inert gases, particularly nitrogen and argon, are vented from the vinyl acetate reactor loop. These gases are introduced with the feed oxygen and in seal purges throughout the unit. Because ethylene is contained in the purge stream, this purge of the inert gases may result in an efficiency loss, controlled by impurities in gases, raw materials, etc, of from about 1% to about 4% of the total ethylene used in the process. In some plants, this inert gas purge stream is simply burned either in a flare or some other device to recover the energy. In these cases, the producer merely accepts the loss rather than attempt to recover the ethylene.

In other plants, the producer may attempt to recover the ethylene. A known way of recovering ethylene is by absorption of the ethylene into vinyl acetate at system pressure followed by depressurizing the absorber residue to recover the absorbed ethylene. Typically, this requires a flash tank in which the pressure can be quickly and dramatically reduced, thus allowing the ethylene to be separated from the vinyl acetate. Once separated from the vinyl acetate, however, the ethylene must be repressurized through the use of a compressor to recover the ethylene and force it back into the reaction loop.

This method requires the use of certain equipment, namely a flash tank and a compressor which, in turn, requires additional equipment and energy cost. Consequently, a method of recovering ethylene requiring less in the way of equipment and energy expenditures remains of interest.

SUMMARY OF THE INVENTION

The method of the present invention eliminates the necessity of a depressurizing step followed by a repressurizing step in order to recover absorbed ethylene in the vinyl acetate process. In the method of the present invention, the ethylene in the inert gas purge stream is absorbed in a stream of acetic acid at system pressure with the absorber residue being fed back into the vinyl acetate reactor loop in either the vaporizer or the recycle gas scrubber. In this way, neither a flash tank nor a compressor is needed.

In accordance with one aspect of the invention, a method for the recovery of ethylene from an inert gas purge stream from a reactor loop in a vapor-phase process for making vinyl acetate is provided. A method of the present invention includes the steps of contacting the inert gas purge stream containing ethylene with acetic acid in an absorption vessel; discharging a stream containing acetic acid and ethylene from the absorption vessel; separating the ethylene from the acetic acid in the stream by contacting the stream with ethylene gas in a scrubber column; and recovering ethylene from a top portion of the scrubber column. The method also includes the step of recycling the recovered ethylene to the reactor loop for further use.

An alternate method of the present invention includes the steps of: contacting the inert gas purge stream containing ethylene with acetic acid in an absorption vessel; discharging a stream containing acetic acid and ethylene from the absorption vessel; and conveying the stream to a vaporizer in the reactor loop for further use.

DESCRIPTION OF SPECIFIC EMBODIMENTS

Figure 1:
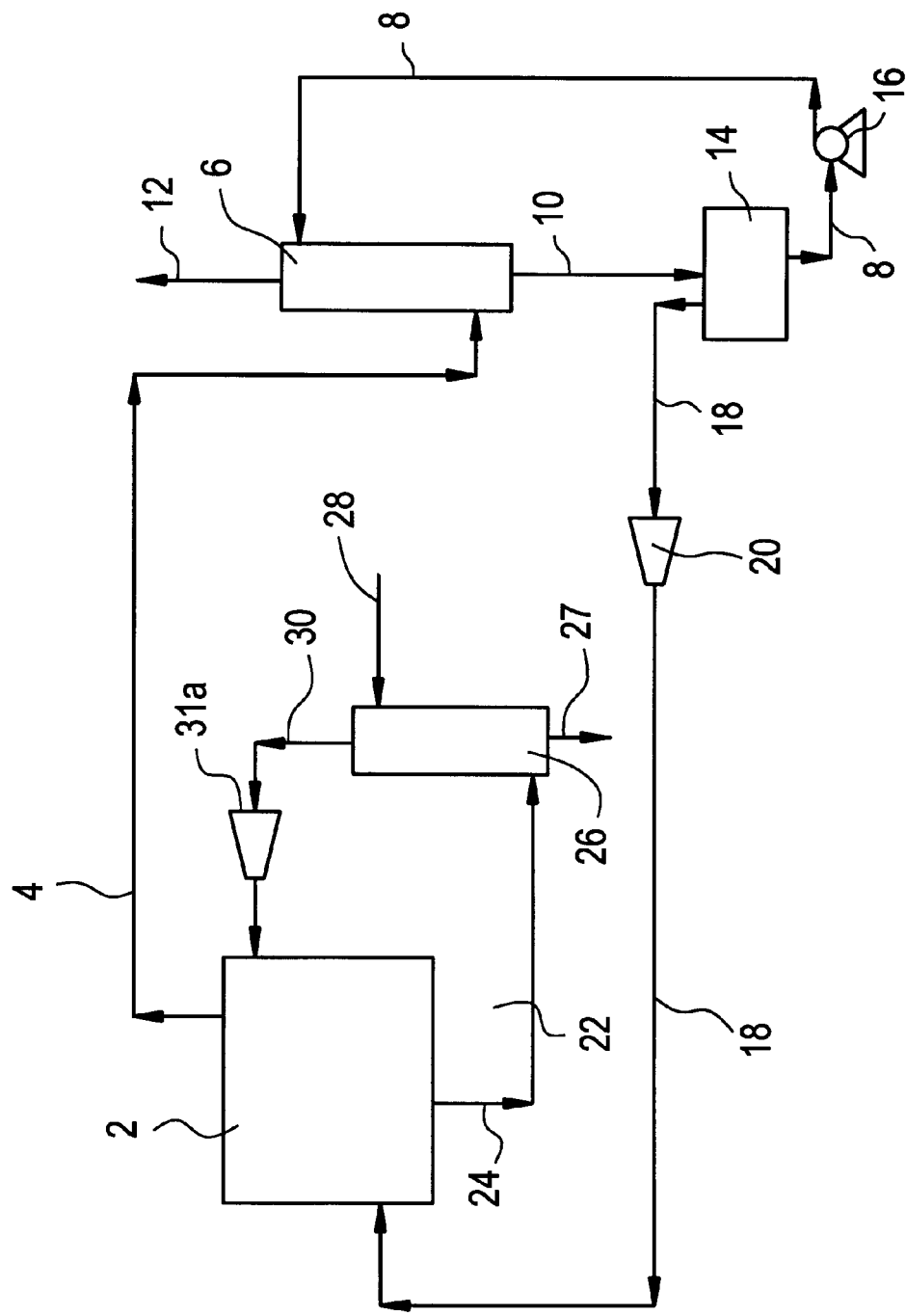
FIG. 1 is a diagrammatic representation of a known method for recovering ethylene from an inert gas purge stream.

Referring to FIG. 1, a prior art method of ethylene recovery, the vinyl acetate reactor loop 2, comprises the aspects of the vinyl acetate process in which the vinyl acetate is actually made, including the vaporizer and reactor (not shown). Typically, vapor-phase processes for the production of vinyl acetate operate at a system pressure ranging from 100–175 psig. The inert gas purge stream 4 is vented from the vinyl acetate reactor loop 2. The inert gas purge stream 4 contains a variety of gases primarily, ethylene, methane, oxygen, nitrogen, and argon. The inert gas purge stream 4 is at system pressure.

Inert gas purge stream 4 is fed into the absorption column 6 where the ethylene is scrubbed from the inert gas purge stream 4 with vinyl acetate from stream 8 which enters absorption column 6 near its top. Absorption column 6 may have trays or packing. Absorption column 6 is operated at up to system pressure. Although discussed as an absorption column, column 6 may also be a simple vessel, with or without internal mechanisms.

Stream 10, comprising the residue from absorption column 6, is discharged from the base of the absorption column 6 and contains primarily vinyl acetate with ethylene selectively absorbed into it. A waste stream 12 is discharged from the top of the absorption column 6 and contains primarily waste gases, namely methane, nitrogen, oxygen, and argon, but may also contain some ethylene. Waste stream 12 may be burned or further processed.

Stream 10, still at system pressure, is conveyed into flash tank 14 where the pressure is substantially less than the system pressure. For example, the pressure in flash tank 14 may be about 5 psig or less. When the pressure is reduced on stream 10 as it enters flash tank 14, the vinyl acetate and ethylene separate.

Stream 8 containing vinyl acetate is discharged from one portion of flash tank 14 and conveyed through a recycle pump 16 back to absorption column 6. Stream 18 is discharged from another portion of flash tank 14 at about atmospheric pressure or lower and contains primarily ethylene. Stream 18 is conveyed to compressor 20 where the ethylene in the stream is repressurized to system pressure and then returned to the vinyl acetate reactor loop 2.

The recycle gas scrubber loop 22 is a part of the vinyl acetate process which is used to remove small amounts of vinyl acetate and acetic acid from reactor effluent gas stream 24. Stream 24, when it reaches recycle gas scrubber column 26, contains gases, namely ethylene, oxygen, nitrogen, and argon, and some entrained liquids, namely acetic acid and vinyl acetate. Stream 24 is fed into scrubber column 26 where it is contacted by acetic acid stream 28 in order to recover the entrained liquids, acetic acid and vinyl acetate. Scrubber column 26 may have trays or packing. The gases from stream 24 are discharged from the top of recycle gas scrubber column 26 and returned to the vinyl acetate reactor loop 2 through line 30 employing recycle compressor 31a. The residue stream 27 from scrubber 26 is called crude vinyl acetate and is comprised mainly of acetic acid, vinyl acetate, water and traces of other components. This crude vinyl acetate is sent to the purification system (not shown) in order to produce specification grade vinyl acetate for sales. Loop 2 as depicted in FIG. 1 contains a reactor, carbon dioxide removal system, and includes line 24.

The ethylene recovery method illustrated in FIG. 1 entails the use of certain equipment, namely flash tank 14 and compressor 20 which, in turn, require additional equipment and energy costs associated with this recovery method. That is, when the ethylene/vinyl acetate stream 10 is depressurized in flash tank 14, thus separating the ethylene from the vinyl acetate, before the ethylene can be returned to the vinyl acetate reactor loop 2, it must be repressurized by compressor 20. Indeed, the ethylene must be repressurized from approximately atmospheric pressure or slightly above the system pressure.

Using the method of the present invention, neither a flash tank nor a compressor is necessary for the operation of the method. Accordingly, the method of the present invention creates obvious savings in equipment and energy costs.

Figure 2:
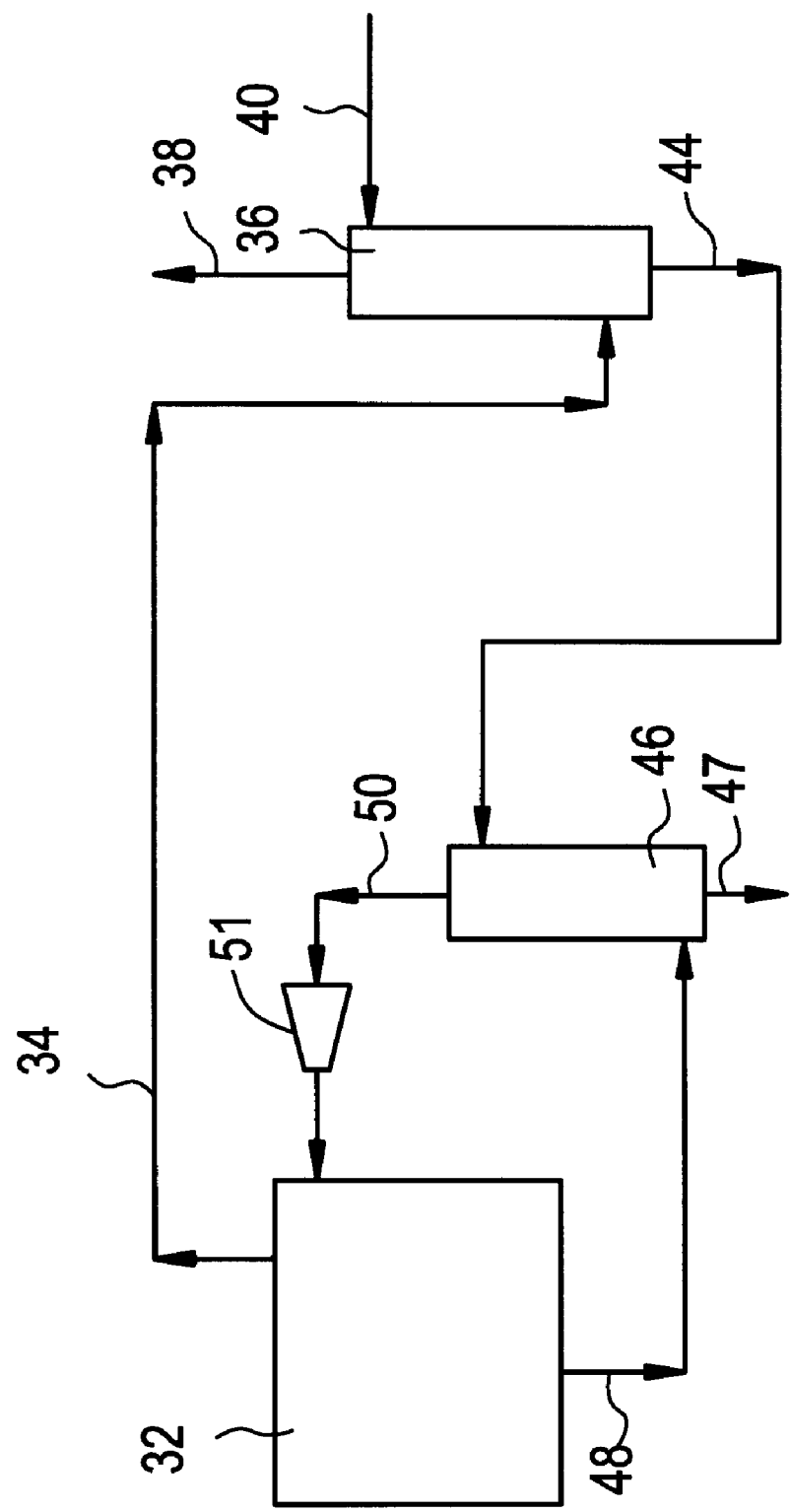
FIG. 2 is a diagrammatic representation of an embodiment of the method of the present invention for recovering ethylene from an inert gas purge stream.

Referring now to FIG. 2, an embodiment of the method of the present invention, vinyl acetate reactor loop 32 comprises the aspects of the vinyl acetate process in which vinyl acetate is produced, including a vaporizer and a reactor (not shown). Inert gas purge stream 34 is vented from the vinyl acetate reactor loop 32. Inert gas purge stream 34 contains a variety of gases, but primarily, ethylene, methane, oxygen, nitrogen, and argon. Inert gas purge stream is at system pressure.

Inert gas purge stream 34 is conveyed into absorption vessel 36 where it is contacted with acetic acid from stream 40. Absorption vessel 36 is operated at system pressure. Absorption vessel 36 may be a column and have trays or packing. Alternatively, absorption vessel 36 may be a contactor, centrifugal contactor, stirred reactor, stirred tank with packing, or the like. Likewise, absorption vessel 36 may be an empty vessel, i.e., having no interior structure but with gas sparging up through the bottom of the vessel.

In absorption vessel 36, ethylene is selectively absorbed into the acetic acid of stream 40 and a stream containing primarily acetic acid and ethylene, is discharged from one aspect of absorption vessel 36 in stream 44. A waste stream 38 is discharged from another aspect of absorption vessel 36 and contains primarily waste gases, namely methane, nitrogen, oxygen, and argon, but may also contain some ethylene. Waste stream 38 may be burned or conveyed for further processing in processes that will be known to those skilled in the art. In certain instances the oxygen content may be high enough to create a flammable mixture. Under these circumstances, methane or other dilutants may be added to column 36 or stream 34 to reduce the oxygen concentration in stream 38 to a non-flammable level.

Acetic acid/ethylene stream 44 is then fed into recycle gas scrubber column 46 near its top. Scrubber column 46 may have trays or packing. The recycle gas scrubber 46 is a part of the vinyl acetate process which is used to remove small amounts of vinyl acetate and acetic acid from the recycle gas stream 48.

Stream 48, when it reaches scrubber column 46, contains gases, namely ethylene, methane, oxygen, nitrogen, and argon, and some entrained liquids, namely acetic acid and vinyl acetate. Stream 48 is fed into the base of scrubber column 46 where it is contacted by acetic acid and ethylene from stream 44. The ethylene is stripped out of stream 44 and discharged from the top of recycle gas scrubber column 46 and returned to the vinyl acetate reactor loop 32 by stream 50 employing compressor 51. Outlet stream 47 is crude vinyl acetate.

In another embodiment of the method of the present invention, stream 44 would be returned to the vaporizer (not shown) in reactor loop 32 from which the ethylene recovered in absorption vessel 36 would be fed to the reactor (also not shown).

This embodiment may require certain special considerations with respect to the acetic acid used in stream 40. The acetic acid may be fresh acid or recycled acid. In many vinyl acetate processes, the acid fed to the recycle gas scrubber column 46 is recycled acetic acid. In order to increase the effectiveness of the acid for absorption purposes, the recycled acid is typically cooled before being fed to recycle gas scrubber column 46.

If this cooled acid is used for this embodiment of the method of the present invention and fed to absorption vessel 36, the resulting residue stream, 44, will also be cooled. Feeding a cooled stream of acid to the vaporizer could increase the energy expenditures necessary for the operation of the vaporizer. Alternatively, the acid in stream 44 could be reheated before feeding it to the vaporizer.

Hot recycled acid could also be used in absorption column 36, however, the effectiveness of the column in absorbing ethylene may suffer. Furthermore, hot acid may be overly corrosive for this application without special metallurgy in the column 36.

The method of the present invention is advantageous because it utilizes equipment already existing in many vinyl acetate processes to recover the ethylene found in the inert gas purge stream 34. Moreover, it does so without the addition of a flash tank or other depressurizing means and without the addition of a compressor or other repressurizing means between the absorption vessel 36 and the vinyl acetate reactor loop 32. Likewise, the recycle acetic acid stream 40 is also present in the vinyl acetate process, and use of this acetic acid stream to scrub the inert gas purge stream 34 does not diminish its effectiveness for use in scrubbing the gas stream 48 in the recycle gas scrubber column 46. Accordingly, the capital and energy cost of using the method of the present invention should be significantly less than that of the method of ethylene recovery depicted in prior art process shown in FIG. 1.

An additional advantage of the method of the present invention is that acetic acid is more selective for ethylene than is vinyl acetate. Thus, as compared with the known method for recovery of ethylene, the present method should be more selective, and thus more effective. Table 1 depicts the solubility of ethylene, nitrogen, and ethylene/nitrogen in vinyl acetate and Table 2 depicts the solubility of ethylene, nitorgen, and ethylene/nitrogen in acetic acid. The data reflect the solubility measured at 30° C. and various pressures expressed as pounds per square inch absolute (psia). The data are reported in grams per liter.

TABLE 1

Solubility of Gases in Vinyl Acetate

| Pressure | Ethylene | Nitrogen | Ethylene/Nitrogen |
|---|---|---|---|
| 45 | 7.2 | 1.4 | 5.1 |
| 105 | 25.1 | 4.3 | 5.8 |
| 165 | 43.2 | 7.1 | 6.1 |

TABLE 2

Solubility of Gases in Acetic Acid

| Pressure | Ethylene | Nitrogen | Ethylene/Nitrogen |
|---|---|---|---|
| 45 | 3.7 | 0.2 | 18.5 |
| 105 | 10.8 | 0.69 | 15.7 |
| 185 | 22.4 | 1.18 | 19.0 |

EXPERIMENTAL CONDITIONS

For Acetic Acid

Approximately 200 ml of acetic acid was loaded into a 300 ml stirred autoclave with heat source and controller. The autoclave had a 161.6 ml blowcase bomb attached to the reactor for gas addition. A 1 liter reservoir was attached to the blowcase; gas was regulated from the reservoir to the blowcase and then into the reactor with a gas regulator. The liquid was degassed by stirring at about 1000 rpms, stopping the stirrer and venting to the atmosphere. The blowcase was then pressurized to an initial pressure of about 400 psig and the valve from the source cylinder was shut off. With the stirrer off the reactor was pressurized to the desired test pressure and gas added until no more is needed to maintain the desired pressure. Once the pressure is stable in the reactor, the test gas is vented following the degassing procedures discussed herein.

For Vinyl Acetate

The procedure discussed above for acetic acid was repeated for study of solubility in vinyl acetate, except that vinyl acetate, due to its volatile nature compared to acetic acid, had to be recharged due to liquid loss.

Continuous purging in the experiment caused some liquid loss and required the recharging of liquid into the reactor. For acetic acid, the reactor had to be recharged two times. For vinyl acetate, the reactor was recharged five times during experimentation. At higher pressures, it was necessary to refill the bomb in order to saturate the liquid. Due to the compressibility of ethylene, the initial pressure was approximated in order to compare data.

When comparing the absorption of both liquids, vinyl acetate dissolved approximately two and a half times more ethylene than acetic acid at the temperatures tested. Gas solubility was found to be better at the lower temperatures for both liquids tested. Although the solubility of gases studied was less in acetic acid than vinyl acetate, the ratio of ethylene solubility to methane or nitrogen solubility was found to be higher for acetic acid than for vinyl acetate.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method for recovery of ethylene from a first, inert gas purge stream containing ethylene and at least one of nitrogen and argon from a reactor loop in a vapor-phase process including a recovery loop, for production of vinyl acetate, the ethylene recovery method comprising:

contacting the first, inert gas purge stream with acetic acid in an absorption vessel to selectively absorb ethylene in the acetic acid;

discharging a second, liquid stream containing acetic acid and ethylene from one portion of the absorption vessel;

discharging out of the recovery loop a third stream containing at least one of nitrogen and argon from another portion of the absorption vessel, wherein the third stream contains less ethylene than the first inert gas stream, separating the ethylene from the acetic acid in the second stream by contacting the second stream with a fourth, recycle gas stream containing ethylene in a scrubber column; and recovering ethylene from the scrubber column.

2. The method of claim 1 further comprising recycling the recovered ethylene from the scrubber column to the reactor loop.

3. The method of claim 1 wherein the third stream further comprises oxygen and wherein at least one diluent is added in an amount sufficient to reduce oxygen concentration in the third stream, whereby the third stream becomes a non-flammable composition.

4. The method of claim 1 further comprising discharging an effluent stream comprising ethylene from the reactor loop, and wherein the fourth, recycle gas stream comprises ethylene recycled from the effluent stream from the reactor loop.

5. A method for recovery of ethylene from a first, inert gas purge stream containing ethylene and at least one of nitrogen and argon from a reactor loop including a vaporizing step in a vapor-phase process including a recovery loop, for production of vinyl acetate, the ethylene recovery method comprising:

contacting the first, inert gas purge stream with acetic acid in an absorption vessel to selectively absorb ethylene in the acetic acid;

discharging a second, liquid stream containing acetic acid and ethylene from one portion of the absorption vessel;

conveying the second stream to the vaporizing step in the reactor loop; and discharging out of the recovery loop a third, waste gas stream containing at least one of nitrogen and argon from another portion of the absorption vessel, wherein the third stream contains less ethylene than the first inert gas stream.

6. The method of claim 5 wherein the third, waste gas stream further comprises oxygen and wherein at least one diluent is added in an amount sufficient to reduce oxygen concentration in the third, waste gas stream whereby the third, waste gas stream becomes a non-flammable composition.

7. A method for recovery of ethylene from a first, inert gas purge stream containing ethylene and at least one of nitrogen and argon from a reactor loop including a vaporizer in a vapor-phase process for production of vinyl acetate, the ethylene recovery method comprising:

contacting the first, inert gas purge stream with acetic acid in an absorption vessel, discharging a second, liquid stream containing acetic acid and ethylene from one portion of the absorption vessel;

conveying the second stream to the vaporizer in the reactor loop; and discharging a third, waste gas stream containing at least one of nitrogen and argon from another portion of the absorption vessel, wherein the third, waste gas stream further comprises oxygen and wherein at least one diluent is added in an amount sufficient to reduce oxygen concentration in the third, waste gas stream whereby the third, waste gas stream becomes a non-flammable composition, and wherein the diluent comprises methane.

8. A method for recovery of ethylene from a first, inert gas purge stream containing ethylene and at least one of nitrogen and argon from a reactor loop in a vapor-phase process for production of vinyl acetate, the ethylene recovery method comprising:

contacting the first, inert gas purge stream with acetic acid in an absorption vessel;

discharging a second, liquid stream containing acetic acid and ethylene from one portion of the absorption vessel;

discharging a third stream containing at least one of nitrogen and argon from another portion of the absorption vessel;

separating the ethylene from the acetic acid in the second stream by contacting the second stream with a fourth, recycle gas stream containing ethylene in a scrubber column; and recovering ethylene from the scrubber column, wherein the third stream further comprises oxygen and wherein at least one diluent is added is an amount sufficient to reduce oxygen concentration in the third stream, whereby the third stream becomes a non-flammable composition, and wherein the diluent comprises methane.

\* \* \* \* \*